US008152116B2

(12) United States Patent
Westberg

(10) Patent No.: US 8,152,116 B2
(45) Date of Patent: Apr. 10, 2012

(54) DIALYSATE BAG SEAL BREAKAGE SENSOR INCORPORATED IN DIALYSATE BAG MANAGEMENT

(75) Inventor: Tom Westberg, Gurnee, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1049 days.

(21) Appl. No.: 12/038,654

(22) Filed: Feb. 27, 2008

(65) Prior Publication Data

US 2009/0212178 A1 Aug. 27, 2009

(51) Int. Cl.
*F16M 11/00* (2006.01)

(52) U.S. Cl. .......... 248/176.1; 604/29; 604/65; 222/103

(58) Field of Classification Search ............... 248/176.1; 604/29, 65, 67, 131; 222/103, 105
See application file for complete search history.

(56) References Cited

U.S. PATENT DOCUMENTS 2,696,963 A * 12/1954 Shepherd ................ 248/229.15
3,804,355 A * 4/1974 Uroshevich ................ 248/124.1
4,055,252 A 10/1977 Klamm et al.
4,182,451 A 1/1980 Watson
4,585,436 A 4/1986 Davis et al.
4,600,401 A 7/1986 Kamen
4,628,186 A 12/1986 Bergemann et al.
4,688,891 A 8/1987 Carratt et al.
4,703,314 A 10/1987 Spani
4,731,053 A * 3/1988 Hoffman ......................... 604/89
4,735,240 A 4/1988 Ziegler
4,744,395 A 5/1988 Ziegler
4,779,460 A 10/1988 Cruickshank
4,801,926 A 1/1989 Bitetti
4,917,155 A 4/1990 Koblasz et al.
4,958,518 A 9/1990 Duenstl et al.
4,994,026 A 2/1991 Fecondini
5,035,865 A 7/1991 Inaba et al.

(Continued)

FOREIGN PATENT DOCUMENTS

WO WO 2005/089832 A2 9/2005

(Continued)

OTHER PUBLICATIONS

International Search Report for International Application No. PCT/US2009/030742 mailed on Apr. 22, 2009.

(Continued)

*Primary Examiner* — Terrell McKinnon
*Assistant Examiner* — Daniel J Breslin
(74) *Attorney, Agent, or Firm* — K&L Gates LLP

(57) ABSTRACT

A stand for a medical fluid treatment, a system for supporting medical fluid bags, and a method for testing and sensing whether a bag or a seal in a chamber of a multi-chamber bag has been broken prior to providing therapy. A stand stores one or more medical fluid bags, each bag stored on a single shelf. Each shelf has a sensor for sensing the presence or absence of fluid in the bag, and reporting the status of the bag to a central location, such as a computer. The sensor can also detect and report on whether fluid has leaked from the bag, or in the case of bags with two or more chambers, if a leak in a frangible seal separating the chambers has developed.

20 Claims, 2 Drawing Sheets

20
14
12
10

U.S. PATENT DOCUMENTS 5,110,076 A * 5/1992 Snyder et al. .............. 248/125.3
5,111,184 A 5/1992 Heaton et al.
5,141,492 A 8/1992 Dadson et al.
5,230,439 A 7/1993 Klok et al.
5,257,985 A 11/1993 Puhl
5,431,496 A 7/1995 Balteau et al.
5,433,704 A * 7/1995 Ross et al. ...................... 604/67
5,524,486 A 6/1996 Hermann
5,533,392 A 7/1996 Kira
5,722,947 A 3/1998 Jeppsson et al.
5,775,540 A * 7/1998 Greenberg .................... 222/102
5,776,345 A 7/1998 Truitt et al.
5,853,388 A * 12/1998 Semel ............................ 604/82
5,894,089 A 4/1999 Ogawa
5,920,967 A * 7/1999 Souza ............................ 24/563
5,921,953 A 7/1999 Novak et al.
5,975,363 A * 11/1999 Haycock ....................... 222/103
6,030,359 A 2/2000 Nowosielski
6,106,612 A 8/2000 White
6,121,555 A 9/2000 Nowosielski et al.
6,186,998 B1 2/2001 Inuzuka et al.
6,202,487 B1 3/2001 Urias et al.
6,219,933 B1 4/2001 Taniguchi et al.
6,277,815 B1 * 8/2001 Knerr ............................ 514/5.5
6,312,074 B1 11/2001 Walker
6,370,951 B1 4/2002 Kerchaert et al.
6,397,674 B1 6/2002 Kerchaert et al.
6,472,887 B1 10/2002 Tullis et al.
6,526,824 B2 3/2003 Chase et al.
6,536,861 B1 3/2003 Usui et al.
6,622,557 B2 9/2003 Petzold
6,663,743 B1 12/2003 Becker et al.
6,690,280 B2 2/2004 Citrenbaum et al.
6,736,006 B2 5/2004 Arias
6,748,164 B1 6/2004 Kuzyk
6,799,820 B1 10/2004 Usui et al.
6,869,158 B2 3/2005 Kojima et al.
6,952,963 B2 10/2005 Delnevo
7,013,727 B2 3/2006 Delnevo
7,055,926 B2 6/2006 Kojima et al.
7,157,727 B2 1/2007 Kimura
7,175,244 B2 2/2007 Usui et al.
7,206,715 B2 4/2007 Vanderveen et al.
7,243,893 B2 7/2007 Sobue et al.
7,267,000 B1 9/2007 Usui et al.
7,270,386 B2 9/2007 Takahashi et al.
7,304,583 B2 12/2007 Beller
D622,377 S * 8/2010 Jackson ....................... D24/128
7,808,246 B2 10/2010 Sobue et al.
7,909,755 B2 3/2011 Itoi
7,909,795 B2 * 3/2011 Childers et al. ............... 604/131
2003/0082069 A1 5/2003 Kuzyk
2004/0019320 A1 1/2004 Childers et al.
2004/0241041 A1 12/2004 Woodworth et al.
2005/0131332 A1 6/2005 Kelly et al.
2005/0133674 A1 * 6/2005 Sobue et al. .................... 248/95
2006/0122576 A1 * 6/2006 Raja et al. .................. 604/890.1
2006/0136095 A1 6/2006 Rob et al.
2006/0154873 A1 7/2006 Sumiyoshi et al.
2007/0276328 A1 11/2007 Childers et al.
2008/0015493 A1 1/2008 Childers et al.
2009/0207218 A1 * 8/2009 Kimura ........................... 347/86
2011/0036864 A1 * 2/2011 McKenna ..................... 222/105

FOREIGN PATENT DOCUMENTS

WO WO 2005/089832 A3 9/2005

OTHER PUBLICATIONS

Written Opinion for International Application No. PCT/US2009/030742 mailed on Apr. 22, 2009.

* cited by examiner

DIALYSATE BAG SEAL BREAKAGE SENSOR INCORPORATED IN DIALYSATE BAG MANAGEMENT

CROSS REFERENCE TO RELATED APPLICATIONS

This application relates to the following co-pending commonly owned patent applications: patent application Ser. No. 11/773,501, entitled "APPARATUS AND METHOD FOR VERIFYING A SEAL BETWEEN MULTIPLE CHAMBERS," filed Jul. 5, 2007 and patent application Ser. No. 11/773,742, entitled "MOBILE DIALYSIS SYSTEM HAVING SUPPLY CONTAINER DETECTION," filed Jul. 5, 2007.

BACKGROUND

The present invention generally relates to dialysis systems. More specifically, the present invention relates to an apparatus and method for sensing whether a chamber in a multi-chamber dialysate bag leaks or has been broken.

Due to disease, injury or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life sustaining. One who has failed kidneys could not continue to live without replacing at least the filtration functions of the kidneys.

Hemodialysis and peritoneal dialysis are two types of dialysis therapies commonly used to treat loss of kidney function. Hemodialysis treatment utilizes the patient's blood to remove waste, toxins and excess water from the patient. The patient is connected to a hemodialysis machine and the patient's blood is pumped through the machine. Catheters are inserted into the patient's veins and arteries to connect the blood flow to and from the hemodialysis machine. As blood passes through a dialyzer in the hemodialysis machine, the dialyzer removes the waste, toxins and excess water from the patient's blood and returns the blood back to the patient. A large amount of dialysate, for example about 120 liters, is used to dialyze the blood during a single hemodialysis therapy. The spent dialysate is then discarded. Hemodialysis treatment lasts several hours and is generally performed in a treatment center about three or four times per week.

Peritoneal dialysis utilizes a dialysis solution or "dialysate", which is infused into a patient's peritoneal cavity through a catheter implanted in the cavity. The dialysate contacts the patient's peritoneal membrane in the peritoneal cavity. Waste, toxins and excess water pass from the patient's bloodstream through the peritoneal membrane and into the dialysate. The transfer of waste, toxins, and water from the bloodstream into the dialysate occurs due to diffusion and osmosis, i.e., an osmotic gradient occurs across the membrane. The spent dialysate drains from the patient's peritoneal cavity and removes the waste, toxins and excess water from the patient. This cycle is repeated.

There are various types of peritoneal dialysis therapies, including continuous ambulatory peritoneal dialysis ("CAPD"), automated peritoneal dialysis and continuous flow peritoneal dialysis. CAPD is a manual dialysis treatment, in which the patient connects an implanted catheter to a drain and allows a spent dialysate fluid to drain from the peritoneal cavity. The patient then connects the catheter to a bag of fresh dialysate and manually infuses fresh dialysate through the catheter and into the patient's peritoneal cavity. The patient disconnects the catheter from the fresh dialysate bag and allows the dialysate to dwell within the cavity to transfer waste, toxins and excess water from the patient's bloodstream to the dialysate solution. After a dwell period, the patient repeats the manual dialysis procedure.

In CAPD the patient performs several drain, fill, and dwell cycles during the day, for example, about four times per day. Each treatment cycle typically takes about an hour. Manual peritoneal dialysis performed by the patient requires a significant amount of time and effort from the patient.

Automated peritoneal dialysis ("APD") is similar to CAPD in that the dialysis treatment includes a drain, fill, and dwell cycle. APD machines, however, automatically perform three to four cycles of peritoneal dialysis treatment, typically overnight while the patient sleeps. The APD machines are fluidly connected to a catheter implanted in the patient. The APD machines are also fluidly connected to a source or bag of fresh dialysate and to a fluid drain.

The APD machines pump fresh dialysate from the dialysate source, through the catheter, into the patient's peritoneal cavity and allow the dialysate to dwell within the cavity so that the transfer of waste, toxins and excess water from the patient's bloodstream to the dialysate solution can take place. The APD machines then pump spent dialysate from the peritoneal cavity, though the catheter, to the drain. APD machines are typically computer controlled so that the dialysis treatment occurs automatically when the patient is connected to the dialysis machine, for example, when the patient sleeps. That is, the APD systems automatically and sequentially pump fluid into the peritoneal cavity, allow for a dwell, pump fluid out of the peritoneal cavity and repeat the procedure.

As with the manual process, several drain, fill, and dwell cycles will occur during APD. A "last fill" is typically used at the end of APD, which remains in the peritoneal cavity of the patient when the patient disconnects from the dialysis machine for the day. APD frees the patient from having to manually performing the drain, dwell, and fill steps.

For each of the above-described dialysis therapies, each of the associated cycles typically consumes a separate bag of solution or dialysate. Over the course of therapy, multiple bags of such solution are used. In many instances, solution bags with a single chamber or pouch are used. In such a case, the solution is completely premixed, sterilized and ready to use. In other instances, the bags include multiple chambers that divide a base solution from an additive. With multi-chamber bags, the patient must break a seal to enable the additive to run to the base solution. It happens sometimes that the patient does not properly open the seal or forgets to open the seal completely. In such a case, therapy does not take place properly. What is needed is a better way to insure that the seal has been broken and the liquids in the chambers properly mixed before use by a patient.

It is therefore desirable to have a ready apparatus to organize and support multiple solutions bags sequentially or simultaneously such that a sensor can determine whether one of the chambers in the bags has been broken prior to use, and thus mixed.

SUMMARY

One embodiment, is a medical fluid supply bag stand. The medical fluid supply bag stand includes a support pole, at least one shelf movably connected to the support pole, the shelf configured for mounting only an upper portion of the medical fluid supply bag, and a sensor mounted on the shelf for sensing liquid in the upper portion of the supply bag, the sensor suitable for determining whether liquid is present in the upper portion.

Another embodiment is a method of sensing a medical fluid. The method includes steps of providing a medical fluid supply bag stand, wherein at least one shelf is movably connected to the stand, the at least one shelf configured for mounting only a portion of a medical fluid supply bag, the medical fluid supply bag having at least two chambers. Another step is mounting only one chamber of the medical fluid supply bag on the at least one shelf, and sensing a presence of the one chamber with a sensor mounted on the at least one shelf. Another step is sensing an absence of liquid in the one chamber if a seal separating the at least two chambers leaks or has been broken.

In another embodiment, the method further comprises connecting the supply bag to a dialysis apparatus selected from the group consisting of: a continuous ambulatory peritoneal dialysis apparatus, an automated peritoneal dialysis apparatus, a hemodialysis apparatus, a hemofiltration apparatus, and a hemodiaflitration apparatus.

Another aspect is a medical fluid supply bag stand. The medical fluid supply bag includes a base, a support pole mounted on the base, and a plurality of shelves in a vertical row, each shelf movably connected to the support pole, and each shelf configured for mounting only a portion of a medical fluid supply bag, and a sensor mounted on each shelf for sensing liquid in an upper portion of the medical fluid supply bag, the sensor suitable for determining whether a leak has developed in the supply bag.

Additional features and advantages are described herein, and will be apparent from, the following Detailed Description and the figures.

DETAILED DESCRIPTION

The present disclosure includes an apparatus and method for supporting one or more medical fluid supply bags during treatment as well as testing such bags to sense and determine whether a seal has been broken, such that fluids flow from one chamber to a second chamber prior to treatment. The stand and method of testing described herein apply to any medical fluid treatment using supply bags having multiple chambers. The apparatus and methods described herein are particularly applicable to dual-chamber bags in which fluids or constituents within the chambers are mixed at the time of therapy. In particular, the stand and test method are well suited for renal failure. For example, the stand and test method are well suited for CAPD, APD, hemodialysis, hemofiltration, hemodiofiltration and any combination thereof. The stand and the method described herein will also suffice for detecting leakage in single-chamber bags.

The present disclosure is intended to address shortcomings in the use of the prior art, such as dual chamber bags made with a heat seal and disclosed by Richmond et al., in U.S. Pat. No. 4,465,488, and Balteau et al., in U.S. Pat. No. 5,431,496, the entire disclosures of which are hereby incorporated by reference in their entirety. As noted, the systems and methods described herein may be used to insure proper mixing of the dialysate liquid components before they are administered to patients. In addition, the seals between chambers can leak and if mixing occurs too soon, the potency and effectiveness of the mixed solution may not be as intended. Accordingly, the present disclosure has discovered unique, inexpensive ways to discover leaks or unintended, premature mixing and to alert users to the situation.

Figure 1A:
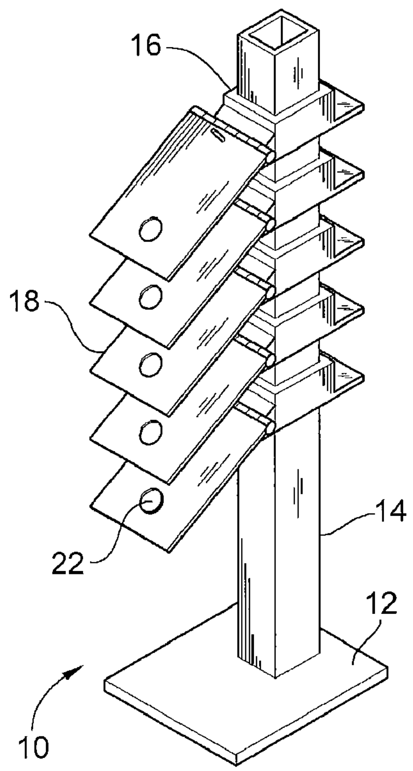
FIG. 1*a* shows a medical fluid bag stand with a vertical row of a plurality of shelves.
Figure 1B:
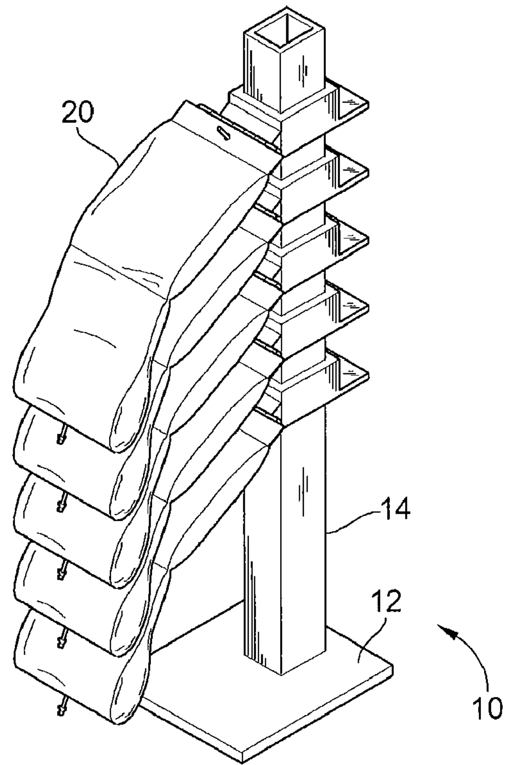
FIG. 1*b* shows the medical fluid bag stand of FIG. 1*a* with a medical fluid bag loaded onto each of a plurality of shelves.

FIGS. 1*a* and 1*b* depict perspective views of a first embodiment of a bag stand. As seen in FIG. 1*a*, the stand 10 includes a base or pedestal 12, a central pole or stand 14, a plurality of shelf supports 16, and a matching plurality of shelves 18 supported on the shelf supports. Each shelf has a sensor 22 for sensing the presence of a container of liquid, such as a 2 L or 5 L bag of dialysis liquid. FIG. 1*b* depicts the same stand 10 with a plurality of bags 20 mounted on the shelves, one bag per shelf.

The stand and its components may be made from metal, such as steel alloys, aluminum or aluminum alloys. These strong materials may be needed for the strength and rigidity of the stand. A 5 L bag of dialysis fluid, containing mostly water, contains about 5 kg (about 11 pounds) of water along with the weight of the package, the seals, tubing, and so forth. A rack with only 5 bags, as depicted in FIG. 1*b*, thus must support over 25 kg (over 55 pounds), in addition to the weight of the shelves, brackets, supports, and so forth. The stand must thus be sturdy. In addition to the metals mentioned above, the stand and its components may be made from plastic, such as engineering plastics, especially fiber-reinforced plastics, such as fiberglass reinforced nylon, and the like.

Figure 2:
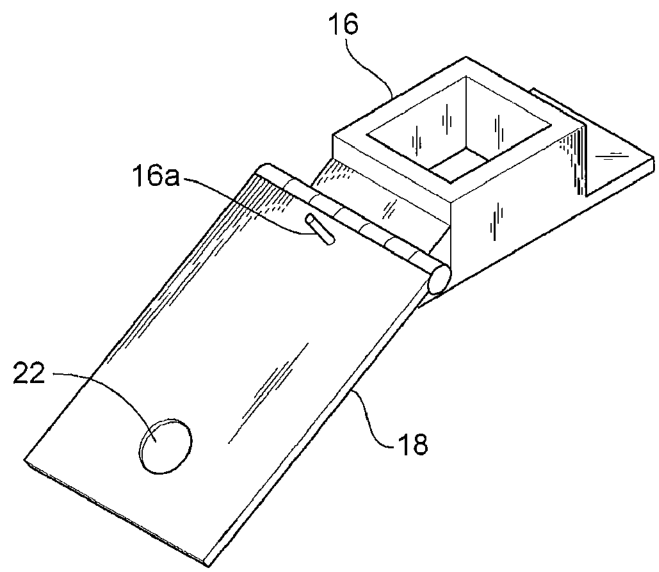
FIG. 2 depicts a shelf according to the embodiment of FIGS. 1*a* and 1*b* with a sensor mounted on the shelf.
Figure 3:
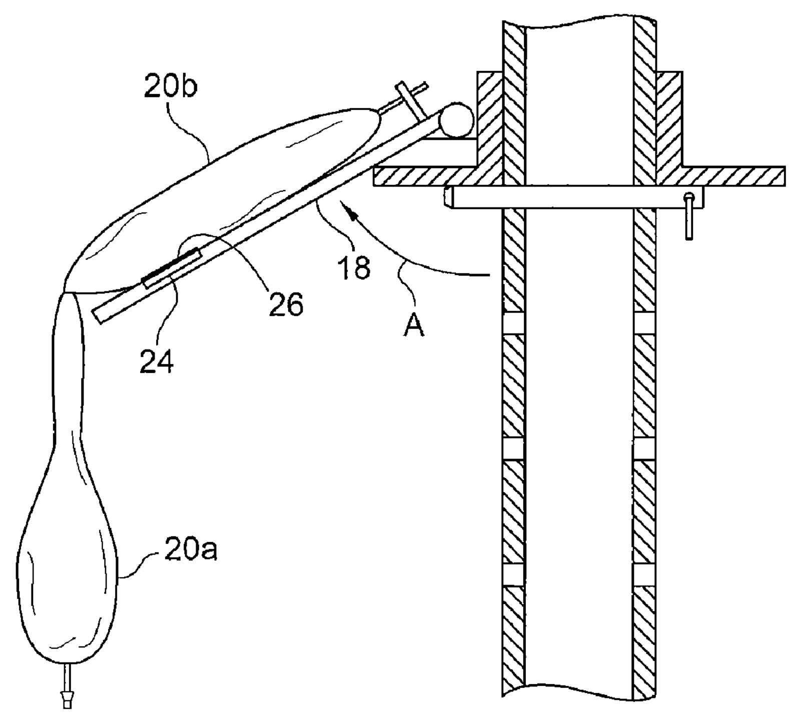
FIG. 3 depicts a side view of the shelf embodiment of FIG. 2.
Figure 4:
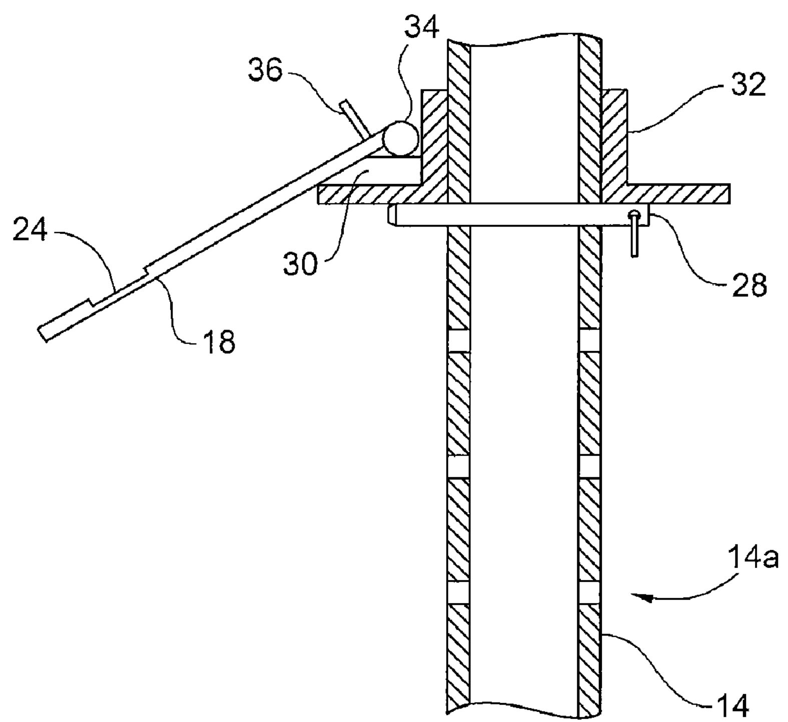
FIG. 4 depicts a more detailed view of a second embodiment of a shelf.

FIGS. 2, 3, and 4 depict closer views of the component parts of the stand. FIG. 2 depicts a shelf support 16 with a hook or attachment for holding an orifice from a bag. Shelf 18 includes a sensor 22 for detecting the presence of a bag on the shelf. The shelf may be made of sheet metal as shown, but instead may be made of sturdy wire or plastic mesh, or other material capable of supporting a bag of dialysis fluid. The sensor is depicted on the top surface of the shelf. However, it is also possible for the sensor to be mounted on the underside of the shelf. As shown below, the shelf may also include an orifice or cutout on its top surface so that the top surface of sensor 22 is flush with the top surface of the shelf. As best shown in FIG. 3, the shelf mounts to the central pole at an acute angle A from vertical.

The sensor may be any sensor capable of sensing a bag of fluid, or a portion of a bag of fluid. As shown in FIG. 1*b*, the bag 20 may rest on the shelf, or as shown in FIG. 3, a lower portion of the bag 20*a* may hang while an upper potion 20*b* rests on the shelf itself. In either version, sensor 22 will sense the presence of the bag 20 or its upper portion 20*b*. Sensor 22 may be a capacitive sensor, sensing the presence of plastic, with a dielectric constant of about 2-6, or water, with a dielectric constant of about 80, rather than air, with a dielectric constant of just over unity. If the frangible or heat seal between the bag portions leaks or is broken so that the liquid may be administered to a patient, the liquid in the upper bag will flow into the lower bag. The sensor will then sense a different dielectric constant after a period of time, such as very quickly for proper mixing, or over several minutes or longer for an inadvertent leak. The sensor is in communication with a system controller or with a separate controller or logic circuit for the bag stand. The change in dielectric constant will be interpreted as a decrease in liquid, due either to proper mixing or to a leak. The controller or logic circuit will send a signal to alert the patient or a caregiver that a decrease has occurred. The decrease in liquid is desirable and required for proper administration of peritoneal dialysis liquid. However, a decrease in liquid at any other time, such as a decrease caused by a leak, is undesirable and should be brought to the attention of the patient or the caregiver.

A capacitive sensor may be calibrated or adjusted to detect this difference as it is positioned on the top side of the shelf or on the bottom side. A bottom side position will not interfere with frequent and rough placement of the bag on the shelf, and may yield longer life for the sensor and the stand. Suitable capacitive sensors include those available from Omron Corporation, Tokyo, Japan. Some sensors are equipped with their own electronics and thus are easy to calibrate and place in service. Capacitive sensors with a sensing range of about 10 mm are excellent in this application.

In addition to capacitive sensors, other suitable sensors include optical sensors that will sense the presence or absence of liquid between a source of light and a light detector. Ultrasonic sensors, which return a signal that depends on reflection of sound waves by an object, are also suitable and may be used. Pressure sensors on a top surface of the shelf, sensing a pressure on the shelf caused by the bag or the upper portion of the bag, may also be used. There are many types of pressure sensors that are suitable for this application.

In this embodiment, shelf stand central pole 16 is in the shape of a hollow square, which is mounted in the base or pedestal, as seen in FIG. 1*a*. Shelf support 16 in this embodiment is shaped as a hollow rectangle with an inside that is slightly larger than the outside of the central pole, so that each shelf support can be placed over the central pole and slid down upon it. As shown in FIG. 4, a pin 28 or other fastener is placed above each shelf support, as it is placed on the pole, the pin used to support the next shelf support that is so placed. Because the shelf supports are only slightly larger than the pole itself, no rocking or back-and-forth motion is possible, and thus only a single pin is needed for each support. Of course, the pin must be able to support the entire shelf, shelf support, and the weight of a bag of liquid, such as a 5 L bag of dialysis fluid.

FIG. 4 depicts a more complete version of a partial cross section of a stand central pole 14, a shelf support 32, and a shelf 18. The central pole 14 includes a plurality of vertically spaced orifices 14*a*, each pair of orifices suitable for insertion of a pin 28, the pin suitable for supporting a shelf support 32, as shown. The shelf support includes a hollow, rectangularly-shaped portion for placing about the central pole 14. The support also includes a support portion 30. Support portion 30 is inclined at an angle from about 30 to 60 degrees from the horizontal and includes a hinge 34 at its upper portion the hinge connecting shelf 18 to the shelf support 28. The shelf includes a hook 36 or other attachment for holding a bag of liquid. As noted previously, shelf 18 may include a recess 24 on its top surface for mounting a sensor, so that a top surface of the sensor is very close to a top surface of the shelf itself. Other shapes may be used. For example, it may be easier to arrange bags if the central pole has a circular cross-section, and each shelf support also has a circularly-shaped inner diameter. With this configuration, each shelf support may be rotatable about the central pole, and it may be easier to place a subsequent bag if each shelf support is easily rotatable and movable.

In use, if the bag contains a frangible or heat seal that breaks, liquid from the upper portion will leak into the lower portion. An ultrasonic or capacitive sensor will detect a lower level of liquid in the bag. A pressure sensor will also detect a lower level of liquid in the bag since a lower pressure will be sensed. If an optical sensor is used, it will more freely pass light at a given distance above the shelf surface. At least the capacitive sensor may be used on the lower surface of the shelf as well as the upper surface of the shelf.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A medical fluid supply bag stand for mounting a medical fluid supply bag for use during a therapy, the medical fluid supply bag including an upper fluid carrying portion and a lower fluid carrying portion, the bag stand including:
- a support pole;
- at least one shelf movably connected to the support pole, the shelf configured for mounting only the upper fluid carrying portion of the medical fluid supply bag, the shelf further configured to support the medical fluid supply bag while in use during the therapy; and
- a sensor mounted on the shelf for sensing liquid in the upper fluid carrying portion of the medical fluid supply bag, the sensor operable during the therapy for determining whether liquid is present in the upper fluid carrying portion.

2. The medical fluid supply bag stand of claim 1, wherein the sensor is a capacitive sensor.

3. The medical fluid supply bag stand of claim 1, wherein the sensor is a pressure sensor, an ultrasonic sensor, or an optical sensor.

4. The medical fluid supply bag stand of claim 1, wherein a portion of the at least one shelf is hingedly mounted to the shelf for swinging out of the way when loading the stand.

5. The medical fluid supply bag stand of claim 1, wherein the sensor detects liquid in the upper fluid carrying portion before fluid in the two fluid carrying portions is mixed and wherein the sensor detects less liquid in the upper fluid carrying portion after liquid in the two fluid carrying portions is mixed.

6. The medical fluid supply bag of claim 1, wherein the at least one shelf is mounted at an acute angle to the support pole.

7. The medical fluid supply bag stand of claim 1, wherein the supply bag is a renal replacement therapy fluid and is configured for connection to a dialysis apparatus selected from the group consisting of: a continuous ambulatory peritoneal dialysis apparatus, an automated peritoneal dialysis apparatus, a hemodialysis apparatus, a hemofiltration apparatus, and a hemodiaflitration apparatus.

8. The medical fluid supply bag stand of claim 1, wherein the at least one shelf comprises a plurality of shelves, and wherein each shelf further comprises a hinge, and the shelf and the hinge are configured for at least a portion of the shelf to swing out of the way for loading a portion of a medical fluid supply bag on each shelf.

9. A method of sensing medical fluid during a medical therapy, the method comprising:

providing a medical fluid supply bag stand, wherein at least one shelf is movably connected to the stand, the at least one shelf configured for mounting only a portion of a medical fluid supply bag for use during the medical therapy, the medical fluid supply bag including an upper fluid carrying portion and a lower fluid carrying portion;

mounting only the upper fluid carrying portion of the medical fluid supply bag on the at least one shelf;

during the medical therapy, sensing a presence of the medical fluid supply bag with a sensor mounted on the at least one shelf; and during the medical therapy, sensing an absence of liquid in the medical fluid supply bag if a seal separating the upper fluid carrying portion and the lower fluid carrying portion leaks or has been broken.

10. The method of claim 9, further comprising sending a signal when a presence of the medical fluid supply bag is sensed.

11. The method of claim 9, further comprising sending a signal if the seal is broken or leaks.

12. The method of claim 9, wherein the sensor is a capacitive or ultrasonic sensor, the sensor detecting a first, higher level of liquid in the bag if the seal is intact and a second, lower level of liquid in the bag if the seal has been broken or leaks.

13. The method of claim 9, further comprising connecting the supply bag to a dialysis apparatus selected from the group consisting of: a continuous ambulatory peritoneal dialysis apparatus, an automated peritoneal dialysis apparatus, a hemodialysis apparatus, a hemofiltration apparatus, and a hemodiaflitration apparatus.

14. The method of claim 9, further comprising loading the upper fluid carrying portion of the medical fluid supply bag on the at least one shelf, so that the sensor detects a presence of only the upper fluid carrying portion of the medical fluid supply bag.

15. A medical fluid supply bag stand for mounting a medical fluid supply bag for use during a therapy, the medical fluid supply bag including an upper fluid carrying portion and a lower fluid carrying portion, the bag stand including:

a base;

a support pole mounted on the base;

a plurality of shelves in a vertical row, each shelf movably connected to the support pole, each shelf configured for mounting only the upper fluid carrying portion of a medical fluid supply bag, each shelf further configured to support one of the medical fluid supply bags while in use during the therapy; and a sensor mounted on each shelf for sensing liquid in the upper fluid carrying portion of the medical fluid supply bag, the sensor operable during the therapy for determining whether liquid is present in the upper fluid carrying portion.

16. The medical fluid supply bag stand of claim 15, wherein the sensor is a capacitive sensor.

17. The medical fluid supply bag stand of claim 15, wherein the sensor detects a thickness of at least about 7 to 10 mm of the medical fluid supply bag and fluid atop the shelf.

18. The medical fluid supply bag stand of claim 15, wherein the support pole comprises a plurality of orifices for mounting supports for the plurality of shelves.

19. The medical fluid supply bag stand of claim 15, wherein each shelf comprises an interface for mounting to the support pole, a mount for a bag support, and a hinge for movably mounting the bag support, and a hook for grasping the medical fluid supply bag.

20. A medical fluid supply bag stand, comprising:

a support pole;

at least one shelf movably connected to the support pole, the shelf configured for mounting only an upper portion of the medical fluid supply bag; and a sensor mounted on the shelf for sensing liquid in the upper portion of the supply bag, the sensor suitable for determining whether liquid is present in the upper portion, wherein the at least one shelf is configured for storing a medical fluid supply bag having at least two chambers, and wherein the sensor detects liquid in an upper chamber before fluid in the two chambers is mixed and wherein the sensor detects less liquid in the upper chamber after liquid in the two chambers is mixed.

* * * * *